(12) United States Patent
Korth et al.

(10) Patent No.: US 7,332,619 B2
(45) Date of Patent: *Feb. 19, 2008

(54) PROCESS FOR THE PREPARATION OF MERCAPTOORGANYL (ALKOXYSILANES)

(75) Inventors: Karsten Korth, Grenzach-Wyhlen (DE); Philipp Albert, Lörrach (DE); Dorit Wolf, Oberursel (DE); Steffen Seebald, Kahl am Main (DE); Reimund Pieter, Bensheim (DE); Alfreg Alig, Geiselbach-Omersbach (DE)

(73) Assignee: Degussa AG, Essen (DE)

( * ) Notice: Subject to any disclaimer, the term of this patent is extended or adjusted under 35 U.S.C. 154(b) by 276 days.

This patent is subject to a terminal disclaimer.

(21) Appl. No.: 11/221,181

(22) Filed: Sep. 7, 2005

(65) Prior Publication Data

US 2006/0052622 A1    Mar. 9, 2006

(30) Foreign Application Priority Data

Sep. 7, 2004  (DE) .................. 10 2004 043 093
May 3, 2005   (DE) .................. 10 2005 020 534

(51) Int. Cl.
*C07F 7/08* (2006.01)

(52) U.S. Cl. ...................... 556/426; 556/627

(58) Field of Classification Search .................. 556/69, 556/427

See application file for complete search history.

(56) References Cited

U.S. PATENT DOCUMENTS

| 5,493,058 | A   |   | 2/1996 | Cadot et al. |
| 6,147,242 | A   |   | 11/2000 | Batz-Sohn |
| 6,433,206 | B1  | * | 8/2002 | Gedon et al. ................ 556/427 |
| 6,777,474 | B2  | * | 8/2004 | Yanagisawa ................ 524/366 |

FOREIGN PATENT DOCUMENTS

EP    1 285 926 A1    2/2003

OTHER PUBLICATIONS

Broadbent, H. Smith et al., "Rhenium Sulfides as Liquid-Phase Hydrogenation Catalysts. A Comparison with Molybdenum Sulfide and Cobalt Polysulfide," Journal of the American Chemical Society, Mar. 20, 1954, pp. 1519-1523, vol. 76, American Chemical Society, Washington, D.C. (XP002227638).

Database Beilstein Online!, Beilstein Institute for Organic Chemistry, Dec. 31, 1996, Frankfurt-Main, Germany (XP002357068).

* cited by examiner

*Primary Examiner*—Yvonne Eyler
*Assistant Examiner*—Yate' K Cutliff
(74) *Attorney, Agent, or Firm*—Robert G. Weilacher; Smith, Gambrell & Russell

(57) ABSTRACT

The invention relates to a process for the preparation of mercaptoorganyl(alkoxysilanes), wherein bis(alkoxysilylorganyl)polysulfides are hydrogenated with hydrogen and a transition metal catalyst in a solvent without the addition of alcohols, $H_2S$ or water.

13 Claims, No Drawings

PROCESS FOR THE PREPARATION OF MERCAPTOORGANYL (ALKOXYSILANES)

The invention relates to a process for the preparation of mercaptoorganyl(alkoxysilanes).

U.S. Pat. No. 6,147,242 discloses a process for the preparation of 3-mercaptopropyl-triethoxysilane by homolytic cleavage of bis(alkoxysilylorganyl)disulfides. The process comprises reaction of bis(alkoxysilylorganyl) disulfides with an alkali metal and a chlorosilane for the preparation of a silylalkylsulfanylsilane intermediate product, which is then converted into the desired mercaptoalkylsilane in the presence of alcohol.

The process has the disadvantages that an additional reagent (chloroalkylsilane) must be used, and of the need to use and dispose of hazardous alkali metal and to isolate the silylalkylsulfanylsilane intermediate product before the alcoholysis step.

U.S. Pat. No. 6,433,206 furthermore discloses a process for the preparation of silicon-containing organomercaptans by hydrogenation of bis(organylsilyl)polysulfides using group VIII metal catalysts, which must be protected against poisoning by means of water, $H_2S$ or alcohols.

This process has the disadvantage that if alcohols which are not the same as the alcohols used for substitution of the alkoxysilanes are used as a poisoning inhibitor or catalyst decontaminating reagent, transesterifications may occur on the silicon atom of the educts used and the products formed. Undesirable silane products of mixed esterification are formed as a result. The addition of decontaminating reagents is therefore limited from practical and economic aspects to those alcohols which are already present in the educt as alkoxysilyl groups.

A further disadvantage of the process is that if alkoxysilanes having long-chain alkoxy substituents (>C8) are used as the starting substance, the working up and distillative removal of the alcohols required as decontaminating reagents becomes increasingly more energy-intensive and therefore technically more demanding and expensive.

The alcohols which function as decontaminating reagents, as oxygen nucleophiles, cannot be employed or are undesirable as indispensable decontaminating reagents during the hydrogenolysis for polysulfanesilanes having any substitution pattern, since they may be responsible for the formation of by-products.

The choice of possible starting substances may be limited by the indispensable use of alcohols as decontaminating reagents. In addition, the known process has the disadvantage that only $H_2S$ or water are available as alternatives to the alcohols. $H_2S$ is a highly toxic gas, the use, storage, metering and disposal of which has a high requirement of caution, risk awareness and plant quality and safety. Water is to be avoided in the case of simultaneous use of alkoxysilanes, since it destroys the starting and product compounds by hydrolysis.

The object of the present invention is to provide a process for the reductive cleavage of bis(alkoxysilylorganyl) polysulfides which takes place without the use of additional decontaminating reagents, such as water, alcohols or hydrogen sulfide, for the metal catalysts required and renders possible a high conversion.

The invention provides a process for the preparation of mercaptoorganyl(alkoxysilanes), which is characterized in that bis(alkoxysilylorganyl)polysulfides are hydrogenated with hydrogen and a transition metal catalyst in a solvent without the addition of alcohols, $H_2S$ or water.

The solvent can be employed in an amount of from 0.1 to 80 wt. %, preferably from 1 to 50 wt. %, very particularly preferably from 1 to 30 wt. %.

The reaction can preferably be carried out with the exclusion of air and water.

The solvents used can have the effect of prolonging the service life of the catalysts used. The solvents used can have the effect of a simpler or improved handling of the catalysts used. The solvents used can increase the reusability of the catalysts used.

The solvents used can have a boiling point of from −50° C. to 250° C., preferably 0-150° C., particularly preferably 20-100° C.

Apart from water and $H_2S$, all non-alcoholic compounds can be employed as the solvent.

Solvents which can be employed are preferably straight-chain, branched or also cyclic non-alcoholic compounds which contain oxygen, sulfur, phosphorus or nitrogen atoms.

Alkanes, ethers, amines, mercaptans, dialkyl sulfides or alkylphosphanes can particularly preferably be employed.

Diethyl ether, methyl tert-butyl ether, tetrahydrofuran, dioxane, carbon dioxide (liquid or as a supercritical fluid), ammonia, pentane, hexane, heptane, octane, DMF or the mercaptoorganyl(alkoxysilanes) formed as products can very particularly preferably be employed.

The solvent can be an ionic liquid or a combination or mixture of ionic liquids.

The ionic liquids used can act as a co-catalyst.

The ionic liquids used can have the effect of an increase in the conversion.

The ionic liquids used can have the effect of an increase in the activity.

The ionic liquids used can have the effect of an increase in the selectivity.

The ionic liquids used can have a melting point of 0-250° C., preferably 50-180° C., particularly preferably 80-150° C.

An ionic liquid can be formed from a homogeneous compound which contains one type of cation and one type of anion. An ionic liquid can be formed from compounds which contain several cation types and several anion types. An ionic liquid can be formed from compounds which contain one cation type and several anion types. An ionic liquid can be formed from compounds which contain several cation types and one anion type.

An ionic liquid can comprise a salt, i.e. at least one cation type and at least one anion type, which is in liquid form under the reaction conditions chosen.

Ionic liquids can have very low vapour pressures (theoretically close to zero), which is advantageous for many uses.

Ionic liquids can comprise organic salts, preferably salts of heterocyclic nitrogen compounds.

Ionic liquids can contain salts of alkylated or polyalkylated heteroaromatics. Alkylated or polyalkylated heteroaromatics can be alkylated pyridines, pyridazines, pyrimidines, pyrazines, imidazoles, pyrazoles, oxazoles or triazoles. The alkyl substituents can have chain lengths of C1-C40 and can be straight-chain, branched or substituted. The alkyl substituents can be identical or different.

Ionic liquids can comprise salts of substituted ammonium $N(alkyl)_3(R')^{(+)}$ or 1,3-dialkylimidazolium ions or phosphonium ions $P\{alkyl\}_3(R')^{(+)}$.

Cations which can be employed are, for example, the cation types bmim, $bm_2im$, emim, ommim, mmim, bupy, $C_6Py$, $C_8Py$, $N_{8,8,8,1}$, $N_{6,2,2,2}$, [MeNEt$_3$], [MeNBu$_3$], [MeNPent$_3$] and [MeNHex$_3$].

The cations can carry one or more positive charges. The anions can carry one or more negative charges.

Anions which can be employed are phosphates, amides, sulfates, tetrachloro(aluminates), sulfites, nitrates, nitrites, alkyl-sulfates, alkylsulfonates or halides.

Anions which can be employed are, for example, chloride, bromide, iodide, $HSO_4^{(-)}$, $BF_4^{(-)}$, $BCl_4^{(-)}$, $PF_6^{(-)}$, $ASF_6^{(-)}$, $SbF_6^{(-)}$, $HCO_3^{(-)}$, lactates, saccharinates, $Al(Cl)_4^{(-)}$, $Al_2(Cl)_7^{(-)}$, $Al_3Cl_{10}^{(-)}$, $CuCl_2^{(-)}$, $Cu_2Cl_3^{(-)}$, $Cu_3Cl_4^{(-)}$, $SnCl_3^{(-)}$, $Sn_2Cl_5^{(-)}$, $CH_3—SO_4^{(-)}$, $CH_3—CH_2—SO_4^{(-)}$, $CF_3—SO_3^{(-)}$, $CH_3—SO_3^{(-)}$, $CF_3—COO^{(-)}$, $C_8H_{17}—(SO_4)^{(-)}$, $C_{16}H_{33}—(SO_4)^{(-)}$, bis[(trifluoromethyl)sulfonyl]amide and tosylate.

Ionic liquids which can be employed are, for example, mixtures of $LiAlCl_4$—$AlCl_3$, $NaAlCl_4$—$AlCl_3$, $KAlCl_4$—$AlCl_3$, $MgAlCl_4$—$AlCl_3$, $NaAlCl_4$—$KAlCl_4$, $NaAlCl_4$—$KAlCl_4$—$AlCl_3$, $NaAlCl_4$—$KAlCl_4$—$MgCl_2$, $KAlCl_4$—$Ca(AlCl_4)_2$ or $NaAlCl_4$—$KAlCl_4$—$LiAlCl_4$. Eutectics of the mixtures or mixtures close to the eutectic point can preferably be employed.

Ionic liquids which can be employed are, for example, $LiAlCl_4$, $NaAlCl_4$, $KAlCl_4$, $Mg\{AlCl_4\}_2$ or $Ca(AlCl_4)_2$.

The cations and anions can correspond to those mentioned by P. Wasserscheid and W. Keim in Angew. Chem. Int. Ed. 2000, 39, 3773.

The cations and anions can correspond to those mentioned by T. Welton in Chem. Rev. 1999, 99, 2071.

The bis(alkoxysilylorganyl)polysulfide to be hydrogenated can be mixed with a polar or non-polar, protic or aprotic substance.

The bis(alkoxysilylorganyl)polysulfides can correspond to a compound of the general formula (I)

$$Z-A-S_x-A-Z \quad (I)$$

wherein x is a number from 1 to 14, preferably 1 to 8, preferably 2 to 4, particularly preferably 2-2.6, Z is identical or different and is $SiX^1X^2X^3$ or $Si(OCH_2—CH_2—)_3N$ and $X^1$, $X^2$, $X^3$ in each case independently of one another can denote hydroxyl (—OH), a linear or branched or cyclic hydrocarbon chain having 1-18 carbon atoms (C1-C18), preferably having C1-C10, preferably methyl, ethyl, propyl or butyl, an alkyl acid $(C_yH_{2y+1})—C(=O)O—$, where y=1-25, or alkenyl acid substituent, for example acetoxy $CH_3—(C=O)O—$, a substituted alkyl or alkenyl acid substituent, a cycloalkane radical having 5-12 carbon atoms, a benzyl radical, a halogen- or alkyl-substituted phenyl radical, alkoxy groups, preferably $(C_1-C_{24})$ alkoxy, having linear or branched hydrocarbon chains, methoxy ($CH_3O—$), ethoxy ($C_2H_5O—$), propoxy ($C_3H_7O—$), butoxy ($C_4H_9O—$), dodecyloxy ($C_{12}H_{25}O—$), tetradecyloxy ($C_{14}H_{29}O—$), hexadecyloxy ($C_{16}H_{33}O—$) or octadecyloxy ($C_{18}H_{37}O—$) being particularly preferred, a cycloalkoxy group having $(C_{5-12})$ atoms, a halogen- or alkyl-substituted phenoxy group, a benzyloxy group, an alkyl ether group $O—(CR^I_2—CR^I_2)—O-Alk$ or an alkyl polyether group $O—(CR^I_2—CR^I_2O)_a-Alk$, where a=2-25, preferably a=2-15, particularly preferably a=3-10, very particularly preferably a=3-6, $R^I$, independently of one another, is H or an alkyl group, preferably a $CH_3$-group, Alk is a linear or branched, saturated or unsaturated alkyl chain having 1-30 carbon atoms (C1-C30), preferably C1-C20, particularly preferably C4-C18, very particularly preferably C8-C16, A is a linear or branched, saturated or unsaturated, aliphatic, aromatic or mixed aliphatic/aromatic divalent hydrocarbon chain comprising $C_1-C_{30}$, preferably $C_1-C_3$, particularly preferably (—$CH_2$—), (—$CH_2$—)$_2$, (—$CH_2$—)$_3$, (—CH($CH_3$)—$CH_2$—) or (—$CH_2$—CH($CH_3$)—).

A can be linear or branched and contain saturated and also unsaturated bonds. A can be provided with the most diverse substituents instead of with hydrogen substituents, such as, for example, —CN, halogens, for example —Cl, —Br or —F, alcohol functionalities —OH or alkoxides. $CH_2$, $CH_2CH_2$, $CH_2CH_2CH_2$, $CH_2CH(CH_3)$, $CH_2CH_2CH_2CH_2$, $CH_2CH_2CH(CH_3)$, $CH_2CH(CH_3)CH_2$, $CH_2CH_2CH_2CH_2CH_2$, $CH_2CH(CH_3)CH_2CH_2$, $CH_2CH_2CH(CH_3)CH_2$, $CH(CH_3)CH_2CH(CH_3)$ or $CH_2CH(CH_3)CH(CH_3)$ can preferably be employed as A.

The following compounds, for example, can be used as the silane of the general formula (I):

$[(MeO)_3Si(CH_2)_3]_2S_2$, $[(MeO)_3Si(CH_2)_3]_2S_3$, $(MeO)_3[Si(CH_2)_3]_2S_4$,
$[(MeO)_3Si(CH_2)_3]_2S_5$, $[(MeO)_3Si(CH_2)_3]_2S_6$, $[(MeO)_3]_2S_7$,
$[(MeO)_3Si(CH_2)_3]_2S_8$, $[(MeO)_3Si(CH_2)_3]_2S_9$, $[(MeO)_3Si(CH_2)_3]_2S_{10}$,
$[(MeO)_3Si(CH_2)_3]_2S_{11}$, $[(MeO)_3Si(CH_2)_3]_2S_{12}$, $[(EtO)_3Si(CH_2)_3]_2S_2$,
$[(EtO)_3Si(CH_2)_3]_2S_3$, $[(EtO)_3Si(CH_2)_3]_2S_4$, $[(EtO)_3Si(CH_2)_3]_3S_5$,
$[(EtO)_3Si(CH_2)_3]_2S_6$, $[(EtO)_3Si(CH_2)_3]_2S_7$, $[(EtO)_3Si(CH_2)_3]_2S_8$,
$[(EtO)_3Si(CH_2)_3]_2S_9$, $[(EtO)_3Si(CH_2)_3]_{[2}S_{10}$, $(EtO)_3Si(CH_2)_3]_2S_{11}$,
$[(EtO)_3Si(CH_2)_3]_2S_{12}$, $[(EtO)_3Si(CH_2)_3]_2S_{13}$,
$[(EtO)_3Si(CH_2)_3]_2S_{14}$, $[(C_3H_7O)_3Si(CH_2)_3]_2S_2$,
$[(C_3H_7O)_3Si(CH_2)_3]_2S_3$, $[(C_3H_7O)_3Si(CH_2)_3]_2S_4$,
$[(C_3H_7O)_3Si(CH_2)_3]_2S_5$, $[(C_3H_7O)_3Si(CH_2)_3]_2S_6$,
$[(C_3H_7O)_3Si(CH_2)_3]_2S_7$, $[(C_3H_7O)_3Si(CH_2)_3]_2S_8$,
$[(C_3H_7O)_3Si(CH_2)_3]_2S_9$, $[(C_3H_7O)_3Si(CH_2)_3]_2S_{10}$,
$[(C_3H_7O)_3Si(CH_2)_3]_2S_{11}$, $[(C_3H_7O)_3Si(CH_2)_3]_2S_{12}$,
$[(C_3H_7O)_3Si(CH_2)_3]_2S_{13}$, $[(C_3H_7O)_3Si(CH_2)_3]_2S_{14}$,
$[(C_{12}H_{25}O)(EtO)_2Si(CH_2)_3]S_x[(CH_2)_3Si(OEt)_3]$,
$[(C_{12}H_{25}O)_2(EtO)Si(CH_2)_3]S_x[(CH_2)_3Si(OEt)_3]$,
$[(C_{12}H_{25}O)_3Si(CH_2)_3]S_x[(CH_2)_3Si(OEt)_3]$,
$[(C_{12}H_{25}O)(EtO)_2Si(CH_2)_3]S_x[(CH_2)_3Si(C_{12}H_{25}O)(OEt)_2]$,
$[(C_{12}H_{25}O)_2(EtO)Si(CH_2)_3]S_x[(CH_2)_3Si(C_{12}H_{25}O)(OEt)_2]$,
$[(C_{12}H_{25}O)_3Si(CH_2)_3]S_x[(CH_2)_3Si(C_{12}H_{25}O)(OEt)_2]$,
$[(C_{12}H_{25}O)(EtO)_2Si(CH_2)_3]S_x[(CH_2)_3Si(C_{12}H_{25}O)_2(OEt)]$,
$[(C_{12}H_{25}O)_2(EtO)Si(CH_2)_3]S_x[(CH_2)_3Si(C_{12}H_{25}O)_2(OEt)]$,
$[(C_{12}H_{25}O)_3Si(CH_2)_3]S_x[(CH_2)_3Si(C_{12}H_{25}O)_2(OEt)]$,
$[(C_{12}H_{25}O)(EtO)_2Si(CH_2)_3]S_x[(CH_2)_3Si(C_{12}H_{25}O)_3]$,
$[(C_{12}H_{25}O)_2(EtO)Si(CH_2)_3]S_x[(CH_2)_3Si(C_{12}H_{25}O)_3]$,
$[(C_{12}H_{25}O)_3Si(CH_2)_3]S_x[(CH_2)_3Si(C_{12}H_{25}O)_3]$,
$[(C_{14}H_{29}O)(EtO)_2Si(CH_2)_3]S_x[(CH_2)_3Si(OEt)_3]$,
$[(C_{14}H_{29}O)_2(EtO)Si(CH_2)_3]S_x[(CH_2)_3Si(OEt)_3]$,
$[(C_{14}H_{29}O)_3Si(CH_2)_3]S_x[(CH_2)_3Si(OEt)_3]$,
$[(C_{14}H_{29}O)(EtO)_2Si(CH_2)_3]S_x[(CH_2)_3Si(C_{14}H_{29}O)(OEt)_2]$,
$[(C_{14}H_{29}O)_2(EtO)Si(CH_2)_3]S_x[(CH_2)_3Si(C_{14}H_{29}O)(OEt)_2]$,
$[(C_{14}H_{29}O)_3Si(CH_2)_3]S_x[(CH_2)_3Si(C_{14}H_{29}O)(OEt)_2]$,
$[(C_{14}H_{29}O)(EtO)_2Si(CH_2)_3]S_x[(CH_2)_3Si(C_{14}H_{29}O)_2(OEt)]$,
$[(C_{14}H_{29}O)_2(EtO)Si(CH_2)_3]S_x[(CH_2)_3Si(C_{14}H_{29}O)_2(OEt)]$,
$[(C_{14}H_{29}O)_3Si(CH_2)_3]S_x[(CH_2)_3Si(C_{14}H_{29}O)_2(OEt)]$,
$[(C_{14}H_{29}O)(EtO)_2Si(CH_2)_3]S_x[(CH_2)3Si(C_{14}H_{29}O)_3]$,
$[(C_{14}H_{29}O)_2(EtO)Si(CH_2)_3]S_x[(CH_2)_3Si(C_{14}H_{29}O)_3]$,
$[(C_{14}H_{29}O)_3Si(CH_2)_3]S_x[(CH_2)_3Si(C_{14}H_{29}O)_3]$,
$[(C_{16}H_{33}O)(EtO)_2Si(CH_2)_3]S_x[(CH_2)_3Si(OEt)_3]$,
$[(C_{16}H_{33}O)_2(EtO)Si(CH_2)_3]S_x[(CH_2)_3Si(OEt)_3]$,
$[(C_{16}H_{33}O)_3Si(CH_2)_3]S_x[(CH_2)_3Si(OEt)_3]$,
$[(C_{16}H_{33}O)(EtO)_2Si(CH_2)_3]S_x[(CH_2)3Si(C_{16}H_{33}O)(OEt)_2]$,
$[(C_{16}H_{33}O)_2(EtO)Si(CH_2)_3]S_x[(CH_2)_3Si(C_{16}H_{33}O)(OEt)_2]$,

[(C$_{16}$H$_{33}$O)$_3$Si(CH$_2$)$_3$]S$_x$[(CH$_2$)$_3$Si(C$_{16}$H$_{33}$O)(OEt)$_2$],
[(C$_{16}$H$_{33}$O)(EtO)$_2$Si(CH$_2$)$_3$]S$_x$[(CH$_2$)$_3$Si(C$_{16}$H$_{33}$O)$_2$(OEt)],
[(C$_{16}$H$_{33}$O)$_2$(EtO)Si(CH$_2$)$_3$]S$_x$[(CH$_2$)$_3$Si(C$_{16}$H$_{33}$O)$_2$(OEt)],
[(C$_{16}$H$_{33}$O)$_3$Si(CH$_2$)$_3$]S$_x$[(CH$_2$)$_3$Si(C$_{16}$H$_{33}$O)$_2$(OEt)],
[(C$_{16}$H$_{33}$O)(EtO)$_2$Si(CH$_2$)$_3$]S$_x$[(CH$_2$)$_3$Si(C$_{16}$H$_{33}$O)$_3$],
[(C$_{16}$H$_{33}$O)$_2$(EtO)Si(CH$_2$)$_3$]S$_x$[(CH$_2$)$_3$Si(C$_{16}$H$_{33}$O)$_3$],
[(C$_{16}$H$_{33}$O)$_3$Si(CH$_2$)$_3$]S$_x$[(CH$_2$)$_3$Si(C$_{16}$H$_{33}$O)$_3$],
[(C$_{18}$H$_{37}$O)(EtO)$_2$Si(CH$_2$)$_3$]S$_x$[(CH$_2$)$_3$Si(OEt)$_3$],
[(C$_{18}$H$_{37}$O)$_2$(EtO)Si(CH$_2$)$_3$]S$_x$[(CH$_2$)$_3$Si(OEt)$_3$],
[(C$_{18}$H$_{37}$O)$_3$Si(CH$_2$)$_3$]S$_x$[(CH$_2$)$_3$Si(OEt)$_3$],
[(C$_{18}$H$_{37}$O)(EtO)$_2$Si(CH$_2$)$_3$]S$_x$[(CH$_2$)$_3$Si(C$_{18}$H$_{37}$O)(OEt)$_2$],
[(C$_{18}$H$_{37}$O)$_2$(EtO)Si(CH$_2$)$_3$]S$_x$[(CH$_2$)$_3$Si(C$_{18}$H$_{37}$O)(OEt)$_2$],
[(C$_{18}$H$_{37}$O)$_3$Si(CH$_2$)$_3$]S$_x$[(CH$_2$)$_3$Si(C$_{18}$H$_{37}$O)(OEt)$_2$],
[(C$_{18}$H$_{37}$O)(EtO)$_2$Si(CH$_2$)$_3$]S$_x$[(CH$_2$)$_3$Si(C$_{18}$H$_{37}$O)$_2$(OEt)],
[(C$_{18}$H$_{37}$O)$_2$(EtO)Si(CH$_2$)$_3$]S$_x$[(CH$_2$)$_3$Si(C$_{18}$H$_{37}$O)$_2$(OEt)],
[(C$_{18}$H$_{37}$O)$_3$Si(CH$_2$)$_3$]S$_x$[(CH$_2$)$_3$Si(C$_{18}$H$_{37}$O)$_2$(OEt)],
[(C$_{18}$H$_{37}$O)(EtO)$_2$Si(CH$_2$)$_3$]S$_x$[(CH$_2$)$_3$Si(C$_{18}$H$_{37}$O)$_3$],
[(C$_{18}$H$_{37}$O)$_2$(EtO)Si(CH$_2$)$_3$]S$_x$[(CH$_2$)$_3$Si(C$_{18}$H$_{37}$O)$_3$] or
[(C$_{18}$H$_{37}$O)$_3$Si(CH$_2$)$_3$]S$_x$[(CH$_2$)$_3$Si(C$_{18}$H$_{37}$O)$_3$].

The bis(alkoxysilylorganyl)polysulfides required as the starting substance can be a mixture of various bis(alkoxysilylorganyl)polysulfides having —S$_1$— to —S$_{14}$— or a bis(alkoxysilylorganyl)polysulfide having a sulfur chain length.

Bis(alkoxysilylorganyl)disulfides having an average chain length of S$_x$=S$_2$ to S$_{2.7}$ (—S$_x$— for x=2-14 can be determined by HPLC or $^1$H-NMR) can preferably be employed as the bis(alkoxysilylorganyl)polysulfides.

The group Z=—SiX$^1$X$^2$X$^3$ can preferably be —Si(OMe)$_3$, —Si(OEt)$_3$, —SiMe(OMe)$_2$, —SiMe(OEt)$_2$, —SiMe$_2$(OMe), —SiMe$_2$(OEt), —Si(OC$_{12}$H$_{25}$)$_3$, Si(OC$_{14}$H$_{29}$)$_3$, Si(OC$_{16}$H$_{33}$)$_3$, Si(OC$_{18}$H$_{37}$)$_3$, Si(OC$_{14}$H$_{29}$)$_2$(OC$_{16}$H$_{33}$), Si(OC$_{14}$H$_{29}$)$_2$(OC$_{18}$H$_{37}$), Si(OC$_{16}$H$_{33}$)$_2$(OC$_{14}$H$_{29}$), Si(OC$_{16}$H$_{33}$)$_2$(OC$_{18}$H$_{37}$), Si(OC$_{18}$H$_{37}$)$_2$(OC$_{16}$H$_{33}$) or Si(OC$_{14}$H$_{29}$)(OC$_{18}$H$_{37}$)$_2$.

Si 266, Si 266/2 Si 261, Si 75 and Si 69 from Degussa AG, Silquest A 1589, Silquest A 1289 or Silquest A 15304 from General Electric-Osi, KBE 846 or KBE 856 from Shin-Etsu Chemical Co. Ltd., Cabrus 4, Cabrus 2A or Cabrus 2B from Daiso Co. Ltd. or HP 669 or HP 1589 from Hung Pai Chemical Company can be employed as the bis(alkoxysilylorganyl)polysulfide.

The bis(alkoxysilylorganyl)polysulfide can contain 0.01 to 5 wt. % of 3-chloroorganyl(alkoxysilane) from the preparation.

The bis(alkoxysilylorganyl)polysulfide can contain 0.001 to 1 wt. % of elemental sulfur from the preparation.

The bis(alkoxysilylorganyl)polysulfide can contain 0.001 to 1 wt. % of alcohol from the preparation.

The mercaptoorganyl(alkoxysilane) formed can be a compound of the general formula (II)

Z-A-SH     (II)

wherein Z and A, in each case independently of one another, have the meaning according to formula (I).

The group —SiX$^1$X$^2$X$^3$ in formula II can preferably be —Si(OMe)$_3$, —Si(OMe)$_2$OH, —Si(OMe)(OH)$_2$, —Si(OEt)$_3$, —Si(OEt)$_2$OH, —Si(OEt)(OH)$_2$, —SiMe(OMe)$_2$, —SiMe(OEt)$_2$), —SiMe(OH)$_2$, —SiMe$_2$(OMe), —SiMe$_2$(OEt), SiMe$_2$(OH), —Si[—O(CO)CH$_3$]$_3$, —Si(OC$_{12}$H$_{25}$)$_3$, Si(OC$_{14}$H$_{29}$)$_3$, Si(OC$_{16}$H$_{33}$)$_3$, Si(OC$_{18}$H$_{37}$)$_3$, Si(OC$_{14}$H$_{29}$)$_2$(OC$_{16}$H$_{33}$), Si(OC$_{14}$H$_{29}$)$_2$(OC$_{18}$H$_{37}$), Si(OC$_{16}$H$_{33}$)$_2$(OC$_{14}$H$_{29}$), Si(OC$_{16}$H$_{33}$)$_2$(OC$_{18}$H$_{37}$), Si(OC$_{18}$H$_{37}$)$_2$(OC$_{16}$H$_{33}$) or Si(OC$_{14}$H$_{29}$)(OC$_{18}$H$_{37}$)$_2$.

The mercaptoorganyl(alkoxysilane) formed can be a mixture of compounds of the general formula (II).

For example, mercaptoorganyl(alkoxysilanes) of the general formula (II) can be:
3-mercaptopropyl(trimethoxysilane),
3-mercaptopropyl(dimethoxyhydroxysilane),
3-mercaptopropyl(triethoxysilane),
3-mercaptopropyl(diethoxyhydroxysilane),
3-mercaptopropyl(diethoxymethoxysilane),
3-mercaptopropyl(tripropoxysilane),
3-mercaptopropyl(dipropoxymethoxysilane),
3-mercaptopropyl(dipropoxyhydroxysilane),
3-mercaptopropyl(tridodecanoxysilane),
3-mercaptopropyl(didodecanoxyhydroxysilane),
3-mercaptopropyl(tritetradecanoxysilane),
3-mercaptopropyl(trihexadecanoxysilane),
3-mercaptopropyl(trioctadecanoxysilane),
3-mercaptopropyl(didodecanoxy)tetradecanoxysilane,
3-mercaptopropyl(dodecanoxy)tetradecanoxy(hexadecanoxy)silane,
3-mercaptopropyl(dimethoxymethylsilane),
3-mercaptopropyl(methoxymethylhydroxysilane),
3-mercaptopropyl(methoxydimethylsilane),
3-mercaptopropyl(hydroxydimethylsilane),
3-mercaptopropyl(diethoxymethylsilane),
3-mercaptopropyl(ethoxyhydroxymethylsilane),
3-mercaptopropyl(ethoxydimethylsilane),
3-mercaptopropyl(dipropoxymethylsilane),
3-mercaptopropyl(propoxymethylhydroxysilane),
3-mercaptopropyl(propoxydimethylsilane),
3-mercaptopropyl(diisopropoxymethylsilane),
3-mercaptopropyl(isopropoxydimethylsilane),
3-mercaptopropyl(dibutoxymethylsilane),
3-mercaptopropyl(butoxydimethylsilane),
3-mercaptopropyl(disiobutoxymethylsilane),
3-mercaptopropyl(siobutoxymethylhydroxysilane),
3-mercaptopropyl(isobutoxydimethylsilane),
3-mercaptopropyl(didodecanoxymethylsilane),
3-mercaptopropyl(dodecanoxydimethylsilane),
3-mercaptopropyl(ditetradecanoxymethylsilane),
3-mercaptopropyl(tetradecanoxymethylhydroxysilane),
3-mercaptopropyl(tetradecanoxydimethylsilane),
2-mercaptoethyl(trimethoxysilane),
2-mercaptoethyl(triethoxysilane),
2-mercaptoethyl(diethoxymethoxysilane),
2-mercaptoethyl(tripropoxysilane),
2-mercaptoethyl(dipropoxymethoxysilane),
2-mercaptoethyl(tridodecanoxysilane),
2-mercaptoethyl(tritetradecanoxysilane),
2-mercaptoethyl(trihexadecanoxysilane),
2-mercaptoethyl(trioctadecanoxysilane),
2-mercaptoethyl(didodecanoxy)tetradecanoxysilane,
2-mercaptoethyl(dodecanoxy)tetradecanoxy(hexadecanoxy)silane,
2-mercaptoethyl(dimethoxymethylsilane),
2-mercaptoethyl(methoxymethylhydroxysilane),
2-mercaptoethyl(methoxydimethylsilane),
2-mercaptoethyl(diethoxymethylsilane),
2-mercaptoethyl(ethoxydimethylsilane),
2-mercaptoethyl(hydroxydimethylsilane),
1-mercaptomethyl(trimethoxysilane),
1-mercaptomethyl(triethoxysilane),
1-mercaptomethyl(diethoxymethoxysilane),
1-mercaptomethyl(diethoxyhydroxysilane),
1-mercaptomethyl(dipropoxymethoxysilane),
1-mercaptomethyl(tripropoxysilane),
1-mercaptomethyl(trimethoxysilane),
1-mercaptomethyl(dimethoxymethylsilane),
1-mercaptomethyl(methoxydimethylsilane), 1-mercaptomethyl(diethoxymethylsilane),
1-mercaptomethyl(ethoxymethylhydroxysilane),
1-mercaptomethyl(ethoxydimethylsilane),
3-mercaptobutyl(trimethoxysilane),
3-mercaptobutyl(triethoxysilane),
3-mercaptobutyl(diethoxymethoxysilane),
3-mercaptobutyl(tripropoxysilane),
3-mercaptobutyl(dipropoxymethoxysilane),
3-mercaptobutyl(dimethoxymethylsilane),
3-mercaptobutyl(diethoxymethylsilane),
3-mercaptobutyl(dimethylmethoxysilane),
3-mercaptobutyl(dimethylethoxysilane),
3-mercaptobutyl(dimethylhydroxysilane),
3-mercaptobutyl(tridodecanoxysilane),
3-mercaptobutyl(tritetradecanoxysilane),
3-mercaptobutyl(trihexadecanoxysilane),
3-mercaptobutyl(didodecanoxy)tetradecanoxysilane,
3-mercaptobutyl(dodecanoxy)tetradecanoxy(hexadecanoxy)silane,
3-mercapto-2-methyl-propyl(trimethoxysilane),
3-mercapto-2-methyl-propyl(triethoxysilane),
3-mercapto-2-methyl-propyl(diethoxymethoxysilane),
3-mercapto-2-methyl-propyl(tripropoxysilane),
3-mercapto-2-methyl-propyl(dipropoxymethoxysilane),
3-mercapto-2-methyl-propyl(tridodecanoxysilane),
3-mercapto-2-methyl-propyl(tritetradecanoxysilane),
3-mercapto-2-methyl-propyl(trihexadecanoxysilane),
3-mercapto-2-methyl-propyl(trioctadecanoxysilane),
3-mercapto-2-methyl-propyl(didodecanoxy)tetradecanoxysilane,
3-mercapto-2-methyl-propyl(dodecanoxy)tetradecanoxy(hexadecanoxy)silane,
3-mercapto-2-methyl-propyl(dimethoxymethylsilane),
3-mercapto-2-methyl-propyl(methoxydimethylsilane),
3-mercapto-2-methyl-propyl(diethoxymethylsilane),
3-mercapto-2-methyl-propyl(ethoxydimethylsilane),
3-mercapto-2-methyl-propyl(hydroxydimethylsilane),
3-mercapto-2-methyl-propyl(dipropoxymethylsilane),
3-mercapto-2-methyl-propyl(propoxydimethylsilane),
3-mercapto-2-methyl-propyl(diisopropoxymethylsilane),
3-mercapto-2-methyl-propyl(isopropoxydimethylsilane),
3-mercapto-2-methyl-propyl(dibutoxymethylsilane),
3-mercapto-2-methyl-propyl(butoxydimethylsilane),
3-mercapto-2-methyl-propyl(disiobutoxymethylsilane),
3-mercapto-2-methyl-propyl(isobutoxydimethylsilane),
3-mercapto-2-methyl-propyl(didodecanoxymethylsilane),
3-mercapto-2-methyl-propyl(dodecanoxydimethylsilane),
3-mercapto-2-methyl-propyl(ditetradecanoxymethylsilane) or
3-mercapto-2-methyl-propyl(tetradecanoxydimethylsilane).

$[(C_9H_{19}O-(CH_2-CH_2O)_2](MeO)_2Si(CH_2)_3SH$,
$[(C_9H_{19}O-(CH_2-CH_2O)_3](MeO)_2Si(CH_2)_3SH$,
$[(C_9H_{19}O-(CH_2-CH_2O)_4](MeO)_2Si(CH_2)_3SH$,
$[(C_9H_{19}O-(CH_2-CH_2O)_5](MeO)_2Si(CH_2)_3SH$,
$[(C_9H_{19}O-(CH_2-CH_2O)_6](MeO)_2Si(CH_2)_3SH$,
$[(C_{12}H_{25}O-(CH_2-CH_2O)_2](MeO)_2Si(CH_2)_3SH$,
$[(C_{12}H_{25}O-(CH_2-CH_2O)_3](MeO)_2Si(CH_2)_3SH$,
$[(C_{12}H_{25}O-(CH_2-CH_2O)_4](MeO)_2Si(CH_2)_3SH$,
$[(C_{12}H_{25}O-(CH_2-CH_2O)_5](MeO)_2Si(CH_2)_3SH$,
$[(C_{12}H_{25}O-(CH_2-CH_2O)_6](MeO)_2Si(CH_2)_3SH$,
$[(C_{13}H_{27}O-(CH_2-CH_2O)_2](MeO)_2Si(CH_2)_3SH$,
$[(C_{13}H_{27}O-(CH_2-CH_2O)_3](MeO)_2Si(CH_2)_3SH$,
$[(C_{13}H_{27}O-(CH_2-CH_2O)_4](MeO)_2Si(CH_2)_3SH$,
$[(C_{13}H_{27}O-(CH_2-CH_2O)_5](MeO)_2Si(CH_2)_3SH$,
$[(C_{13}H_{27}O-(CH_2-CH_2O)_6](MeO)_2Si(CH_2)_3SH$,
$[(C_{14}H_{29}O-(CH_2-CH_2O)_2](MeO)_2Si(CH_2)_3SH$,
$[(C_{14}H_{29}O-(CH_2-CH_2O)_3](MeO)_2Si(CH_2)_3SH$,
$[(C_{14}H_{29}O-(CH_2-CH_2O)_4](MeO)_2Si(CH_2)_3SH$,
$[(C_{14}H_{29}O-(CH_2-CH_2O)_5](MeO)_2Si(CH_2)_3SH$,
$[(C_{14}H_{29}O-(CH_2-CH_2O)_6](MeO)_2Si(CH_2)_3SH$,
$[(C_9H_{19}O-(CH_2-CH_2O)_2]_2(MeO)Si(CH_2)_3SH$,
$[(C_9H_{19}O-(CH_2-CH_2O)_3]_2(MeO)Si(CH_2)_3SH$,
$[(C_9H_{19}O-(CH_2-CH_2O)_4]_2(MeO)Si(CH_2)_3SH$,
$[(C_9H_{19}O-(CH_2-CH_2O)_5]_2(MeO)Si(CH_2)_3SH$,
$[(C_9H_{19}O-(CH_2-CH_2O)_6]_2(MeO)Si(CH_2)_3SH$,
$[(C_{12}H_{25}O-(CH_2-CH_2O)_2]_2(MeO)Si(CH_2)_3SH$,
$[(C_{12}H_{25}O-(CH_2-CH_2O)_3]_2(MeO)Si(CH_2)_3SH$,
$[(C_{12}H_{25}O-(CH_2-CH_2O)_4]_2(MeO)Si(CH_2)_3SH$,
$[(C_{12}H_{25}O-(CH_2-CH_2O)_5]_2(MeO)Si(CH_2)_3SH$,
$[(C_{12}H_{25}O-(CH_2-CH_2O)_6]_2(MeO)Si(CH_2)_3SH$,
$[(C_{13}H_{27}O-(CH_2-CH_2O)_2]_2(MeO)Si(CH_2)_3SH$,
$[(C_{13}H_{27}O-(CH_2-CH_2O)_3]_2(MeO)Si(CH_2)_3SH$,
$[(C_{13}H_{27}O-(CH_2-CH_2O)_4]_2(MeO)Si(CH_2)_3SH$,
$[(C_{13}H_{27}O-(CH_2-CH_2O)_5]_2(MeO)Si(CH_2)_3SH$,
$[(C_{13}H_{27}O-(CH_2-CH_2O)_6]_2(MeO)Si(CH_2)_3SH$,
$[(C_{14}H_{29}O-(CH_2-CH_2O)_2]_2(MeO)Si(CH_2)_3SH$,
$[(C_{14}H_{29}O-(CH_2-CH_2O)_3]_2(MeO)Si(CH_2)_3SH$,
$[(C_{14}H_{29}O-(CH_2-CH_2O)_4]_2(MeO)Si(CH_2)_3SH$,
$[(C_{14}H_{29}O-(CH_2-CH_2O)_5]_2(MeO)Si(CH_2)_3SH$,
$[(C_{14}H_{29}O-(CH_2-CH_2O)_6]_2(MeO)Si(CH_2)_3SH$,
$[(C_9H_{19}O-(CH_2-CH_2O)_2](EtO)_2Si(CH_2)_3SH$,
$[(C_9H_{19}O-(CH_2-CH_2O)_3](EtO)_2Si(CH_2)_3SH$,
$[(C_9H_{19}O-(CH_2-CH_2O)_4](EtO)_2Si(CH_2)_3SH$,
$[(C_9H_{19}O-(CH_2-CH_2O)_5](EtO)_2Si(CH_2)_3SH$,
$[(C_9H_{19}O-(CH_2-CH_2O)_6](EtO)_2Si(CH_2)_3SH$,
$[(C_{12}H_{25}O-(CH_2-CH_2O)_2](EtO)_2Si(CH_2)_3SH$,
$[(C_{12}H_{25}O-(CH_2-CH_2O)_3](EtO)_2Si(CH_2)_3SH$,
$[(C_{12}H_{25}O-(CH_2-CH_2O)_4](EtO)_2Si(CH_2)_3SH$,
$[(C_{12}H_{25}O-(CH_2-CH_2O)_5](EtO)_2Si(CH_2)_3SH$,
$[(C_{12}H_{25}O-(CH_2-CH_2O)_6](EtO)_2Si(CH_2)_3SH$,
$[(C_{13}H_{27}O-(CH_2-CH_2O)_2](EtO)_2Si(CH_2)_3SH$,
$[(C_{13}H_{27}O-(CH_2-CH_2O)_3](EtO)_2Si(CH_2)_3SH$,
$[(C_{13}H_{27}O-(CH_2-CH_2O)_4](EtO)_2Si(CH_2)_3SH$,
$[(C_{13}H_{27}O-(CH_2-CH_2O)_5](EtO)_2Si(CH_2)_3SH$,
$[(C_{13}H_{27}O-(CH_2-CH_2O)_6](EtO)_2Si(CH_2)_3SH$,
$[(C_{14}H_{29}O-(CH_2-CH_2O)_2](EtO)_2Si(CH_2)_3SH$,
$[(C_{14}H_{29}O-(CH_2-CH_2O)_3](EtO)_2Si(CH_2)_3SH$,
$[(C_{14}H_{29}O-(CH_2-CH_2O)_4](EtO)_2Si(CH_2)_3SH$,
$[(C_{14}H_{29}O-(CH_2-CH_2O)_5](EtO)_2Si(CH_2)_3SH$,
$[(C_{14}H_{29}O-(CH_2-CH_2O)_6](EtO)_2Si(CH_2)_3SH$,
$[(C_9H_{19}O-(CH_2-CH_2O)_2]_2(EtO)Si(CH_2)_3SH$,
$[(C_9H_{19}O-(CH_2-CH_2O)_3]_2(EtO)Si(CH_2)_3SH$,
$[(C_9H_{19}O-(CH_2-CH_2O)_4]_2(EtO)Si(CH_2)_3SH$,
$[(C_9H_{19}O-(CH_2-CH_2O)_5]_2(EtO)Si(CH_2)_3SH$,
$[(C_9H_{19}O-(CH_2-CH_2O)_6]_2(EtO)Si(CH_2)_3SH$,
$[(C_{12}H_{25}O-(CH_2-CH_2O)_2]_2(EtO)Si(CH_2)_3SH$,
$[(C_{12}H_{25}O-(CH_2-CH_2O)_3]_2(EtO)Si(CH_2)_3SH$,
$[(C_{12}H_{25}O-(CH_2-CH_2O)_4]_2(EtO)Si(CH_2)_3SH$,
$[(C_{12}H_{25}O-(CH_2-CH_2O)_5]_2(EtO)Si(CH_2)_3SH$,
$[(C_{12}H_{25}O-(CH_2-CH_2O)_6]_2(EtO)Si(CH_2)_3SH$,
$[(C_{13}H_{27}O-(CH_2-CH_2O)_2]_2(EtO)Si(CH_2)_3SH$,
$[(C_{13}H_{27}O-(CH_2-CH_2O)_3]_2(EtO)Si(CH_2)_3SH$,
$[(C_{13}H_{27}O-(CH_2-CH_2O)_4]_2(EtO)Si(CH_2)_3SH$,
$[(C_{13}H_{27}O-(CH_2-CH_2O)_5]_2(EtO)Si(CH_2)_3SH$,
$[(C_{13}H_{27}O-(CH_2-CH_2O)_6]_2(EtO)Si(CH_2)_3SH$,
$[(C_{14}H_{29}O-(CH_2-CH_2O)_2]_2(EtO)Si(CH_2)_3SH$,
$[(C_{14}H_{29}O-(CH_2-CH_2O)_3]_2(EtO)Si(CH_2)_3SH$,
$[(C_{14}H_{29}O-(CH_2-CH_2O)_4]_2(EtO)Si(CH_2)_3SH$,
$[(C_{14}H_{29}O-(CH_2-CH_2O)_5]_2(EtO)Si(CH_2)_3SH$,
$[(C_{14}H_{29}O-(CH_2-CH_2O)_6]_2(EtO)Si(CH_2)_3SH$,
$[(C_9H_{19}O-(CH_2-CH_2O)_2]_3Si(CH_2)_3SH$,
$[(C_9H_{19}O-(CH_2-CH_2O)_3]_3Si(CH_2)_3SH$,
$[(C_9H_{19}O-(CH_2-CH_2O)_4]_3Si(CH_2)_3SH$,
$[(C_9H_{19}O-(CH_2-CH_2O)_5]_3Si(CH_2)_3SH$,

[(C$_9$H$_{19}$O—(CH$_2$—CH$_2$O)$_6$]$_3$Si(CH$_2$)$_3$SH,
[(C$_{12}$H$_{25}$O—(CH$_2$—CH$_2$O)$_2$]$_3$Si(CH$_2$)$_3$SH,
[(C$_{12}$H$_{25}$O—(CH$_2$—CH$_2$O)$_3$]$_3$Si(CH$_2$)$_3$SH,
[(C$_{12}$H$_{25}$O—(CH$_2$—CH$_2$O)$_4$]$_3$Si(CH$_2$)$_3$SH,
[(C$_{12}$H$_{25}$O—(CH$_2$—CH$_2$O)$_5$]$_3$Si(CH$_2$)$_3$SH,
[(C$_{12}$H$_{25}$O—(CH$_2$—CH$_2$O)$_6$]$_3$Si(CH$_2$)$_3$SH,
[(C$_{13}$H$_{27}$O—(CH$_2$—CH$_2$O)$_2$]$_3$Si(CH$_2$)$_3$SH,
[(C$_{13}$H$_{27}$O—(CH$_2$—CH$_2$O)$_3$]$_3$Si(CH$_2$)$_3$SH,
[(C$_{13}$H$_{27}$O—(CH$_2$—CH$_2$O)$_4$]$_3$Si(CH$_2$)$_3$SH,
[(C$_{13}$H$_{27}$O—(CH$_2$—CH$_2$O)$_5$]$_3$Si(CH$_2$)$_3$SH,
[(C$_{13}$H$_{27}$O—(CH$_2$—CH$_2$O)$_6$]$_3$Si(CH$_2$)$_3$SH,
[(C$_{14}$H$_{29}$O—(CH$_2$—CH$_2$O)$_2$]$_3$Si(CH$_2$)$_3$SH,
[(C$_{14}$H$_{29}$O—(CH$_2$—CH$_2$O)$_3$]$_3$Si(CH$_2$)$_3$SH,
[(C$_{14}$H$_{29}$O—(CH$_2$—CH$_2$O)$_4$]$_3$Si(CH$_2$)$_3$SH,
[(C$_{14}$H$_{29}$O—(CH$_2$—CH$_2$O)$_5$]$_3$Si(CH$_2$)$_3$SH,
[(C$_{14}$H$_{29}$O—(CH$_2$—CH$_2$O)$_6$]$_3$Si(CH$_2$)$_3$SR or
HS—CH$_2$—CH$_2$—CH$_2$—Si(OCH$_2$—CH$_2$—)$_3$N.

The process according to the invention can be carried out under hydrogenolysis conditions.

The hydrogenation can be carried out under a hydrogen pressure of from 5 to 250 bar, preferably 10 to 200 bar, particularly preferably 10 to 99 bar, very particularly preferably 10 to 75 bar excess pressure.

The hydrogenation can be carried out at a temperature of from 50 to 250° C., preferably 75 to 199° C., particularly preferably 100 to 175° C., very particularly preferably 110 to 170° C.

The reaction time for the hydrogenation can be less than 300 minutes, preferably less than 270 minutes, particularly preferably less than 240 minutes, very particularly preferably less than 210 minutes.

Additives can be added to the reaction mixture before, during or at the end of the reaction.

The additives can have the effect of prolonging the service life of the catalysts used. The additives can have the effect of a simpler or improved handling of the catalysts used. The additives can increase the reusability of the catalysts used. The additives can improve the profitability of the process.

Additives can be organosulfur compounds, titanium alkoxylates, amines, organic or inorganic acids or bases or mixtures thereof.

Additives can be carboxylic acids, DMSO, monoalkylamines, dialkylamines or trialkylamines. Additives can be Ti(OC$_4$H$_9$)$_4$ or Ti(OC$_3$H$_7$)$_4$.

The transition metal catalyst can be a catalyst, the catalytically active component of which comprises one or more metals of group VIII. Nickel, cobalt, rhodium, ruthenium, palladium, iridium or platinum can be employed as the catalytically active components.

The catalytically active component can additionally be doped or contain additional components, such as, for example, alkali metals, preferably Li, Na, K or Rb, alkaline earth metals, preferably Be, Mg, Ca, Sr or Ba, elements of main group 3, preferably B, Al, Ga or In, elements of main group 4, preferably C, Si, Ge, Sn or Pb, elements of main group 5, preferably N, P, As or Sb, elements of main group 6, preferably O, S, Se or Te, elements of main group 7, preferably F, Cl, Br or I, or subgroup elements, preferably Sc, Y, Ti, Zr, Hf, V, Nb, Ta, Cr, Mo, W, Mn, Re, Fe, Ru, Co, Rh, Ir, Ni, Pd, Pt, Cu, Ag, Au, Zn or Cd.

A preferred doping component can be a hydride, oxide, halide, for example fluoride, chloride, bromide or iodide, sulfide or nitride.

The doped transition metal catalysts can be porous skeleton catalysts of the Raney type which are doped with transition metals and/or transition metal compounds, for example molybdenum.

The doped transition metal catalysts can be porous, activated metal catalysts of the Raney type which are doped with transition metals and/or transition metal compounds, for example molybdenum. The doped transition metal catalysts can preferably be activated nickel metal catalysts of the Raney type which are doped with transition metals and/or transition metal compounds, for example molybdenum.

The weight content of the doping component (present in elemental form or as a chemical compound), based on the weight of the doped transition metal catalyst, can be 0.00001 to 80 wt. %, preferably 0.0001 to 50 wt. %, particularly preferably 0.001 to 15 wt. %, very particularly preferably 0.01 to 7.5 wt. %.

The catalytically active component can comprise a finely divided, non-supported, activated metal. The activated, non-supported metal can be employed as a solid, in suspension or embedded in waxes or oils.

The catalytically active component can be applied to one of the known and conventional catalyst support materials, such as, for example, diatomaceous earth, carbon, silica, active charcoals, kieselguhr, alumina or alumosilicate.

The catalyst concentration, based on the catalytically active metal, can be 0.0001 to 1 mmol per 1 g of bis (alkoxysilylorganyl)polysulfide.

Preferably, for cobalt as the active metal, the catalyst concentration, based on the catalytically active metal, can be from 0.001 to 1 mmol, particularly preferably 0.008 to 0.5 mmol, very particularly preferably 0.01 to 0.1 mmol, per 1 g of bis(alkoxysilylorganyl)polysulfide.

Preferably, for nickel as the active metal, the catalyst concentration, based on the catalytically active metal, can be from 0.001 to 1 mmol, particularly preferably 0.01 to 1 mmol, very particularly preferably 0.1 to 0.9 mmol, per 1 g of bis(alkoxysilylorganyl)polysulfide.

Preferably, for ruthenium as the active metal, the catalyst concentration, based on the catalytically active metal, can be from 0.001 to 1 mmol, particularly preferably 0.005 to 0.5 mmol, very particularly preferably 0.005 to 0.1 mmol, per 1 g of bis(alkoxysilylorganyl) polysulfide.

Preferably, for rhodium as the active metal, the catalyst concentration, based on the catalytically active metal, can be from 0.001 to 1 mmol, particularly preferably 0.005 to 0.5 mmol, very particularly preferably 0.005 to 0.1 mmol, per 1 g of bis(alkoxysilylorganyl)polysulfide.

Preferably, for palladium as the active metal, the catalyst concentration, based on the catalytically active metal, can be from 0.001 to 1 mmol, particularly preferably 0.005 to 1 mmol, very particularly preferably 0.05 to 1 mmol, per 1 g of bis(alkoxysilylorganyl)polysulfide.

Preferably, for iridium as the active metal, the catalyst concentration, based on the catalytically active metal, can be from 0.001 to 1 mmol, particularly preferably 0.005 to 0.5 mmol, very particularly preferably 0.005 to 0.1 mmol, per 1 g of bis(alkoxysilylorganyl)polysulfide.

Preferably, for platinum as the active metal, the catalyst concentration, based on the catalytically active metal, can be from 0.001 to 1 mmol, particularly preferably 0.005 to 0.5 mmol, very particularly preferably 0.005 to 0.1 mmol, per 1 g of bis(alkoxysilylorganyl)polysulfide.

A parameter which can serve for comparison of the rate of the hydrogenolysis at a given temperature T and a constant pressure p is the conversion which can be expressed quantitatively by the relationship "conversion of educt" per "mmol of catalyst metal" per "minute".

If the conversion can be increased at lower temperatures, this is a considerable improvement from the ecological, energy and economic aspect. The energy efficiency of the process increases at decreased temperatures, the space/time yield increases with the conversion, and a simplified handling of the substances employed and obtained often results at decreased temperatures or pressures. The loading on the industrial plant decreases at lower temperatures and pressures.

The conversion can be 0.001 to 10 g of bis(alkoxysilylorganyl)polysulfide per 1 mmol of catalytically active metal per minute.

Preferably, for cobalt as the active metal, the conversion can be 0.001 to 10 g, particularly preferably 0.01 to 10 g, very particularly preferably 0.1 to 5 g of bis(alkoxysilylorganyl)polysulfide per 1 mmol of catalytically active metal per minute.

Preferably, for nickel as the active metal, the conversion can be 0.001 to 10 g, particularly preferably 0.01 to 10 g, very particularly preferably 0.1 to 5 g of bis(alkoxysilylorganyl)polysulfide per 1 mmol of catalytically active metal per minute.

Preferably, for ruthenium as the active metal, the conversion can be 0.001 to 10 g, particularly preferably 0.01 to 5 g, very particularly preferably 0.1 to 3 g of bis(alkoxysilylorganyl)polysulfide per 1 mmol of catalytically active metal per minute.

Preferably, for rhodium as the active metal, the conversion can be 0.001 to 10 g, particularly preferably 0.01 to 5 g, very particularly preferably 0.1 to 3 g of bis(alkoxysilylorganyl)polysulfide per 1 mmol of catalytically active metal per minute.

Preferably, for palladium as the active metal, the conversion can be 0.001 to 10 g, particularly preferably 0.01 to 5 g, very particularly preferably 0.1 to 3 g of bis(alkoxysilylorganyl)polysulfide per 1 mmol of catalytically active metal per minute.

Preferably, for iridium as the active metal, the conversion can be 0.01 to 10 g, particularly preferably 0.1 to 5 g, very particularly preferably 0.15 to 3 g of bis(alkoxysilylorganyl)polysulfide per 1 mmol of catalytically active metal per minute.

Preferably, for platinum as the active metal, the conversion can be 0.01 to 10 g, particularly preferably 0.1 to 5 g, very particularly preferably 0.5 to 5 g of bis(alkoxysilylorganyl)polysulfide per 1 mmol of catalytically active metal per minute.

A parameter which can serve for comparison of the rate of the hydrogenolysis at a given temperature T and a constant pressure p is the molar conversion which can be expressed quantitatively by the relationship "product formed in mmol" per "catalytically active metal" per "minute".

The molar conversion can be 0.001 to 50 mmol of mercaptoorganyl(alkoxysilane) per 1 mmol of catalytically active metal per minute.

Preferably, for transition metal catalysts comprising iron, nickel, cobalt, ruthenium, rhodium, platinum, iridium or palladium, the molar conversion can be 0.001 to 50 mmol, preferably 0.01 to 40 mmol, particularly preferably 0.05 to 30 mmol, very particularly preferably 0.1 to 20 mmol of mercaptoorganyl(alkoxysilane) per 1 mmol of transition metal of group VIII present per minute.

With the process according to the invention, more than 90 per cent by weight, preferably more than 92 percent by weight, particularly preferably more than 94 percent by weight, very particularly preferably more than 96 percent by weight of the bis(alkoxysilylorganyl)polysulfide employed can be converted into a mercaptoorganyl(alkoxysilane).

With the process according to the invention, the relative content (mol %) of the bis(alkoxysilylorganyl)monosulfide present can remain constant.

With the process according to the invention, the relative content (mol %) of the bis(alkoxysilylorganyl)monosulfide present can increase.

With the process according to the invention, the relative content (mol %) of the bis(alkoxysilylorganyl)monosulfide present can decrease.

In the process according to the invention, the relative content of the bis(alkoxysilylorganyl)monosulfide contained in the educt can be <10 wt. %, preferably <8 wt. %, particularly preferably <6 wt. %, very particularly preferably <4 wt. %.

The process according to the invention can be a batch process or a continuous process.

The batch process can be a slurry process or suspension process, for example in stirred autoclaves or Buss reactors.

The continuous processes can be a slurry process with a continuous liquid and gas feed.

Known reactors for gas/liquid/solid reactions can be employed in the continuous process. Typical representatives can be the trickle and sump reactor for fixed bed reactors and the stirred tank, the bubble column and the fluidized bed for suspension reactors.

The process according to the invention has the advantage that the hydrogenolysis of the polysulfides can also be carried out successfully under milder conditions than described by the prior art, without the use of highly toxic $H_2S$ or alcohols. No adverse impairment of the hydrogenation by dispensing with specific decontaminating reagents can be found.

A satisfactory activity for cleavage of bis(alkoxysilylorganyl)polysulfides by $H_2$ with the catalysts used can be achieved with the process according to the invention.

The use of decontaminating reagents can be dispensed with in the process according to the invention.

Compared with the prior art of hydrogenation of bis(alkoxysilylorganyl)polysulfides in bulk in the absence of decontaminating reagents, conversions which are twice as high can be obtained, for example, for ruthenium. These higher conversions can already be obtained under milder reaction conditions in respect of temperature and pressure than have been described hitherto in the prior art for polysulfanesilane systems without decontaminating reagents. By a higher conversion, not only is the space/time yield improved considerably, the specific energy consumption for the preparation of mercaptoorganyl(alkoxysilanes) by reductive cleavage with $H_2$ from bis(alkoxysilylorganyl)polysulfides is also reduced. By a lower energy consumption and milder reaction conditions, the loading on the plant is lower and, inter alia, less wear results. By a lower energy consumption in the preparation of mercaptoorganyl(alkoxysilanes), the energy balance of the process is improved and there is less stress on the environment.

EXAMPLES

The comparison examples from U.S. Pat. No. 6,433,206 are summarized in Table 1. A disulfanesilane mixture which chiefly comprises bis(3-triethoxysilylpropyl)disulfide and is not specified in more detail is employed as the polysulfanesilane.

The formation of by-products is not described. The products are analysed by gas chromatography methods which are not described in more detail.

TABLE 1

Comparison examples

| No. | Conditions Temperature °C | Pressure psig | Pressure bar | Catalyst | Substance ratios Amount of catalyst g | Amount of metal on catalyst g | Molar amount of metal on catalyst mmol | Amount of poly-sulfane-silane g | Time Time min | Product composition SH wt. % | S1 wt. % | S2 wt. % | Sx wt. % | Conversion Amount of silane reacted to catalyst metal per minute g/mmol/min | Mass balance Total product silane wt. % |
|---|---|---|---|---|---|---|---|---|---|---|---|---|---|---|---|
| 1 | 190 | 620 | 104.16 | 55% Ni on kieselguhr | 2 | 1.1 | 18.7 | 591.4 | 60 | 11.2 | 9.5 | 69.4 | 7.3 | 0.059 | 97.4 |
|   |   |   |   |   |   |   |   |   | 120 | 18.4 | 9 | 63 | 7.2 | 0.048 | 97.6 |
|   |   |   |   |   |   |   |   |   | 180 | 30.7 | 8.5 | 52.6 | 5 | 0.054 | 96.8 |
| 5 | 190 | 600 | 100.8 | 55% Ni on kieselguhr | 5 | 2.75 | 46.9 | 502 | 60 | 13.6 | 8.9 | 62.5 | 7.3 | 0.024 | 92.3 |
|   |   |   |   |   |   |   |   |   | 120 | 30.7 | 7.8 | 49.8 | 3 | 0.027 | 91.3 |
|   |   |   |   |   |   |   |   |   | 1800 | 44 | 7.5 | 36.2 | 0 | 0.026 | 87.7 |
| 6 | 200 | 600 | 100.8 | 55% Ni on kieselguhr | 5 | 2.75 | 46.9 | 490 | 60 | 18.2 | 8.4 | 62 | 5.7 | 0.032 | 94.3 |
|   |   |   |   |   |   |   |   |   | 120 | 39 | 8 | 45.9 | 1.6 | 0.034 | 94.5 |
|   |   |   |   |   |   |   |   |   | 1800 | 57 | 7.88 | 28.7 | 0 | 0.033 | 93.6 |
| 3 | 190 | 300 | 50.4 | 55% Ni on kieselguhr | 5 | 2.75 | 46.9 | 547 | 60 | 10.8 | 8.33 | 65.4 | 9.7 | 0.021 | 94.2 |
|   |   |   |   |   |   |   |   |   | 1200 | 39.1 | 7.94 | 44.9 | 1.6 | 0.038 | 93.5 |
| 4 | 190 | 1000 | 168 | 55% Ni on kieselguhr | 5 | 2.75 | 46.9 | 503 | 60 | 17.8 | 8.69 | 60.2 | 8 | 0.032 | 94.7 |
|   |   |   |   |   |   |   |   |   | 120 | 66.5 | 7.9 | 20.7 | 0 | 0.059 | 95.1 |
| 2 | 100 | 1400 | 235.2 | 5% Pd/C | 4 | 0.2 | 1.9 | 637 | 60 | 1.9 | 9.8 | 89.1 | 1.2 | 0.107 | 102.0 |

The examples according to the invention based on a disulfanesilane are summarized in Table 2, 3 and 4. Si 266 (commercial product from Degussa AG/[bis(alkoxysilylorganyl)disulfide]) is hydrogenated catalytically according to the conditions in Table 2, 3 and 4 in an apparatus from Chemscan, which comprises 8 autoclaves which are heated in parallel by means of an oil bath, the reactor volumes of which are 20 ml and which are equipped with anchor-type magnetic stirrers which rotate at 1,300 rpm on a fixed shaft in the centre of the reactor.

The reaction is ended after the stated times.

In the "Product composition" columns in Table 2, 3 and 4, only the components mercaptopropyl(triethoxysilane), bis(triethoxysilylpropyl)disulfide, bis(triethoxysilylpropyl) trisulfide and bis(triethoxysilylpropyl)tetrasulfide are taken into account. Bis(triethoxysilylpropyl)monosulfide and 3-chloropropyl(triethoxysilane) are ignored.

The product composition is determined by means of $^1$H-NMR.

According to combined GC/HPLC and NMR analyses, the Si 266 used for the experiments contains 1.7 wt. % bis(triethoxysilylpropyl)monosulfide, 84 wt. % bis(triethoxysilylpropyl)disulfide, 12 wt. % bis(triethoxysilylpropyl) trisulfide and 1 wt. % bis(triethoxysilylpropyl)tetrasulfide.

The average chain length determined for the polysulfane mixture is approx. 2.14 (only the mean of S2-S8 is taken into account). The Si 266 used contains 0.8 wt. % 3-chloropropyl (triethoxysilane).

TABLE 2

| No. | Catalyst type | Weight of catalyst mg | Amount of metal based on catalyst mg | Amount of metal based on catalyst mmol | Silane concentration (g/l) | Amount of silane g | Temperature °C | Pressure bar | Reaction time min | Product composition SH wt. % | S2 wt. % | S3 wt. % | S4 wt. % | Conversion (Amount of silane reacted to amount of catalyst per min) g/mmol/min |
|---|---|---|---|---|---|---|---|---|---|---|---|---|---|---|
| 1 | H 105 BA/W 5% Ru | 100.4 | 5.02 | 0.0497 | 200/dioxane | 1.2 | 174 | 95 | 205 | 100 | 0 | 0 | 0 | 0.118 |
| 2 | H 105 BA/W 5% Ru | 52.6 | 2.63 | 0.0260 | 200/dioxane | 1.2 | 176 | 95 | 205 | 100 | 0 | 0 | 0 | 0.225 |

TABLE 3

| No. | Catalyst | Weight of catalyst mg | Amount of metal on catalyst mg | Amount of metal on catalyst mmol | Concentration of Si 266 in 1 kg of mixture g/kg | Amount of Si 266 g | Temperature °C. | Pressure bar | Reaction time min | Product composition SH wt. % | S2 wt. % | S3 wt. % | S4 wt. % | Conversion (Amount of silane reacted to amount of catalyst per minute) g/mmol/min |
|---|---|---|---|---|---|---|---|---|---|---|---|---|---|---|
| 3 | H 105 BA/W 5% Ru | 50 | 2.5 | 0.0247 | 555/SH | 3 | 163 | 94 | 198 | 68.9 | 31.1 | 0.0 | 0.0 | 0.153 |
| 4 | H 105 BA/W 5% Ru | 50 | 2.5 | 0.0247 | 555/SH | 3 | 157 | 51 | 347 | 56.0 | 44.0 | 0.0 | 0.0 | 0.042 |
| 5 | CE 105 R/W 5% Pd + 0.5% Mo | 50 | 2.5 | 0.023 | 555/SH | 3 | 162 | 95 | 198 | 65.8 | 34.2 | 0.0 | 0.0 | 0.140 |
| 6 | CE 105 R/W 5% Pd + 0.5% Mo | 50 | 2.5 | 0.023 | 555/SH | 3 | 159 | 52 | 347 | 55.7 | 44.3 | 0.0 | 0.0 | 0.043 |
| 7 | G-49 B/55 wt. % Ni | 50 | 27.5 | 0.468 | 555/SH | 3 | 157 | 61 | 198 | 71.0 | 29.0 | 0.0 | 0.0 | 0.009 |
| 8 | G-96 B/66 wt. % Ni + alkaline promoters | 50 | 33 | 0.562 | 555/SH | 3 | 153 | 86 | 198 | 100.0 | 0.0 | 0.0 | 0.0 | 0.015 |

TABLE 4

| No. | Catalyst type | Weight of catalyst mg | Amount of metal based on catalyst mg | Amount of metal based on catalyst mmol | Silane concentration (g/l) | Amount of Si 266 g | Temperature °C. | Pressure bar | Reaction time min | Product composition SH wt. % | S2 wt. % | S3 wt. % | S4 wt. % | Conversion (Amount of silane reacted per amount of catalyst per min) mg/mmol/min |
|---|---|---|---|---|---|---|---|---|---|---|---|---|---|---|
| 9 | E 105 RS/W 5% Pd | 99.8 | 4.99 | 0.047 | 400/cyclohexane | 2.4 | 168 | 50 | 360 | 100 | 0 | 0 | 0 | 0.142 |
| 10 | E 105 RS/W 5% Pd | 85.8 | 4.29 | 0.040 | 200/cyclohexane | 1.2 | 170 | 50 | 220 | 86 | 14 | 0 | 0 | 0.116 |
| 11 | CE 105 R/W 5% Pd + 0.5% Mo | 100.2 | 5.01 | 0.047 | 400/cyclohexane | 2.4 | 157 | 50 | 360 | 95 | 5 | 0 | 0 | 0.134 |
| 12 | CE 105 R/W 5% Pd + 0.5% Mo | 50.4 | 2.52 | 0.024 | 200/cyclohexane | 1.2 | 167 | 50 | 417 | 94 | 6 | 0 | 0 | 0.114 |
| 13 | H 105 BA/W 5% Ru | 99.3 | 4.965 | 0.049 | 500/cyclohexane | 3 | 168 | 50 | 485 | 100 | 0 | 0 | 0 | 0.126 |
| 14 | H 105 BA/W 5% Ru | 100.4 | 5.02 | 0.050 | 400/cyclohexane | 2.4 | 173 | 50 | 360 | 100 | 0 | 0 | 0 | 0.134 |
| 15 | H 105 BA/W 5% Ru | 50.2 | 2.51 | 0.025 | 200/cyclohexane | 1.2 | 164 | 95 | 321 | 88 | 12 | 0 | 0 | 0.132 |

The examples according to the invention based on a tetrasulfanesilane are summarized in Table 5. Si 69 (commercial product from Degussa AG/[bis(alkoxysilylorganyl) tetrasulfide]) is hydrogenated catalytically according to the conditions in Table 5, in an apparatus from Chemscan, which comprises 8 autoclaves which are heated in parallel by means of an oil bath, the reactor volumes of which are 20 ml and which are equipped with anchor-type magnetic stirrers which rotate at 1,300 rpm on a fixed shaft in the centre of the reactor.

The reaction is ended after the stated times.

In the "Product composition" columns in Table 5, only the components mercaptopropyl(triethoxysilane), bis(triethoxysilylpropyl)disulfide, bis(triethoxysilylpropyl)trisulfide and bis(triethoxysilylpropyl)tetrasulfide are taken into account. Bis(triethoxysilylpropyl)monosulfide and 3-chloropropyl(triethoxysilane) are ignored.

The product composition stated is determined by means of $^1$H-NMR.

According to combined GC/HPLC and NMR analyses, the Si 69 used for the experiments contains 0.1 wt. % bis(triethoxysilylpropyl)monosulfide, 17 wt. % bis(triethoxysilylpropyl)disulfide, 27 wt. % bis(triethoxysilylpropyl)trisulfide, 25 wt. % bis(triethoxysilylpropyl)tetrasulfide and approx. 29 wt. % bis(triethoxysilylpropyl)polysulfide with $-S_x-x \geq 5$.

The average chain length determined for the polysulfane mixture is 3.75. The Si 69 contains 1.4 wt. % 3-chloropropyl (triethoxysilane).

TABLE 5

| No. | Catalyst type | Weight of catalyst mg | Amount of metal based on catalyst mg | Amount of metal based on catalyst mmol | Silane concentration [g/l] | Amount of Si 69 g | Temperature [° C.] | Pressure [bar] | Reaction time after min | Product composition SH wt. % | S2 wt. % | S3 wt. % | S4 wt. % | Conversion (silane per amount of catalyst per minute) g/mmol/min |
|---|---|---|---|---|---|---|---|---|---|---|---|---|---|---|
| 16 | H 105 BA/W 5% Ru | 50.0 | 2.5 | 0.025 | 300/dioxane | 1.8 | 168 | 64 | 400 | 68.2 | 24.5 | 7.3 | 0.0 | 0.124 |
| 17 | H 105 BA/W 5% Ru | 50.0 | 2.5 | 0.025 | 300/dioxane | 1.8 | 164 | 89.1 | 411 | 69.3 | 21.1 | 9.6 | 0.0 | 0.123 |

The abbreviations contained in the tables have the following meanings: SH=3-mercaptopropyl(triethoxysilane), S2=bis(triethoxysilylpropyl)disulfide, S3=bis(triethoxysilylpropyl)trisulfide, S4=bis(triethoxysilylpropyl)tetrasulfide.

Si 69 [bis(alkoxysilylorganyl)tetrasulfide] and Si 266 [bis(alkoxysilylorganyl)disulfide] are commercially available bis(alkoxysilylorganyl)polysulfides from Degussa AG.

The catalysts with the abbreviations H 105 BA/W 5% Ru, E 105 RS/W 5% Pd, CE 105 R/W 5% Pd+0.5% Mo and E 105 Y/W 5% Pd are noble metal powdered catalysts which are prepared by application of a noble metal component, such as ruthenium or palladium, to a porous support material of high surface area. The content of the noble metal component here is 5 wt. %, based on the dry weight of the catalyst. The catalysts are employed as pulverulent, free-flowing solids. The catalysts mentioned are supported on active charcoal.

The catalyst with the abbreviation B 111 W was an activated metal catalyst which is prepared by suspending finely divided elemental nickel in aqueous solution. The catalyst is employed as a pulverulent solid after the metal component has been separated off.

The catalysts with the abbreviations contain the following amounts of active metal: H 105 BA/W 5% Ru, E 105 RS/W 5% Pd, CE 105 R/W 5% Pd+0.5% Mo, E 105 Y/W 5% Pd, and B 111 W 100% Ni. The catalysts G-96 B and T 8027 are commercial products from Süd-Chemie AG. The catalyst G-96 B contains 66% nickel and alkaline promoters.

The catalyst T 8027 contains 52% nickel and 2.4% zirconium.

A DRX 500 NMR apparatus from Bruker, inter alia, is used for analysis of the products according to the rules and operating conditions known to the person skilled in the art. The measurement frequencies are 99.35 MHz for $^{29}$Si nuclei and 500.13 MHz for $^{1}$H nuclei. Tetramethylsilane (TMS) serves as the reference.

The analysis of bis(alkoxysilylorganyl)polysulfides and mercaptoorganyl(alkoxysilanes) and mixtures thereof can be carried out by GC, HPLC and NMR (U. Görl, J. Münzenberg, D. Luginsland, A. Müller Kautschuk Gummi Kunststoffe 1999, 52(9), 588, D. Luginsland Kautschuk Gummi Kunststoffe 2000, 53(1-2), 10 and M. W. Backer et al, Polmer Preprints 2003, 44(1), 245).

The use of decontaminating reagents can be dispensed with in the process according to the invention.

Compared with the prior art of hydrogenation of bis(alkoxysilylorganyl)polysulfides in bulk in the absence of decontaminating reagents, conversions which are twice as high can be obtained for ruthenium.

The invention claimed is:

1. Process for the preparation of mercaptoorganyl(alkoxysilanes), characterized in that bis(alkoxysilylorganyl)polysulfides are hydrogenated with hydrogen and a transition metal catalyst in a solvent without the addition of alcohols, H$_2$S or water.

2. Process for the preparation of mercaptoorganyl(alkoxysilanes) according to claim 1, characterized in that the bis(alkoxysilylorganyl)polysulfide is a compound of the general formula (I)

$$Z\text{-}A\text{-}S_x\text{-}A\text{-}Z \qquad (I)$$

wherein x is a number from 1 to 14

Z is identical or different and is SiX$^1$X$^2$X$^3$ or Si(OCH$_2$—CH$_2$—)$_3$N, X$^1$, X$^2$, X$^3$ in case independently of one another can denote hydroxyl (—OH), a linear or branched or cyclic hydrocarbon chain having 1-18 carbon atoms (C1-C18), an alkyl acid (C$_y$H$_{2y+1}$)—C(=O)O—, where y=1-25,or alkenyl acid substituent, a substituted alkyl or alkenyl acid substituent, a cycloalkane radical having 5-12 carbon atoms, a benzyl radical, a halogen- or alkyl-substituted phenyl radical, alkoxy groups with (C$_1$-C$_{24}$)alkoxy, having linear or branched hydrocarbon chains, a cycloalkoxy group having (C$_{5-12}$) atoms, a halogen- or alkyl-substituted phenoxy group, a benzyloxy group, an alkyl ether group O—(CR$^1_2$—CR$^1_2$)—O-Alk or an alkyl polyether group O—(CR$^1_2$—CR$^1_2$O)$_a$-Alk, where a=2-25, R$^1$, independently of one another, is H or an alkyl group, Alk is a linear or branched, saturated or unsaturated alkyl chain having 1-30 carbon atoms (C1-C30), A is a linear or branched, saturated or unsaturated, aliphatic, aromatic or mixed aliphatic/aromatic divalent hydrocarbon chain comprising C1-C30.

3. Process for the preparation of mercaptoorganyl(alkoxysilanes) according to claim 2, characterized in that the bis(alkoxysilylorganyl)polysulfides are mixtures of compounds of the general formula (I).

4. Process for the preparation of mercaptoorganyl(alkoxysilanes) according to claim 1, characterized in that the bis(alkoxysilylorganyl)polysulfide to be hydrogenated is mixed with a polar or non-polar, protic or aprotic substance.

5. Process for the preparation of mercaptoorganyl(alkoxysilanes) according to claim 1, characterized in that the hydrogenation is carried out under a pressure of from 10 to 250 bar.

6. Process for the preparation of mercaptoorganyl(alkoxysilanes) according to claim 1, characterized in that the hydrogenation is carried out at a temperature of from 50 to 250° C.

7. Process for the preparation of mercaptoorganyl(alkoxysilanes) according to claim 1, characterized in that the catalyst contains nickel, cobalt, rhodium, ruthenium, palladium, iridium or platinum as the catalytically active component.

8. Process for the preparation of mercaptoorganyl(alkoxysilanes) according to claim 1, characterized in that the catalytically active component is additionally doped or contains additional components.

9. Process for the preparation of mercaptoorganyl(alkoxysilanes) according to claim 8, characterized in that the catalytically active component comprises one or more alkali metals, alkaline earth metals, elements of main group 3, elements of main group 4, elements of main group 5, elements of main group 6, elements of main group 7 or subgroup elements.

10. Process for the preparation of mercaptoorganyl(alkoxysilanes) according to claim 1, characterized in that the catalyst concentration, based on the catalytically active metal, is 0.0001 to 1 mmol per 1 g of bis(alkoxysilylorganyl) polysulfide.

11. Process for the preparation of mercaptoorganyl(alkoxysilanes) according to claim 1, characterized in that the process is carried out batchwise.

12. Process for the preparation of mercaptoorganyl(alkoxysilanes) according to claim 1, characterized in that it is carried out continuously.

13. Process for the preparation of mercaptoorganyl(alkoxysilanes) according to claim 1, characterized in that the reaction mixture contains additives.

* * * * *